US005573950A

United States Patent [19]
Graessle et al.

[11] Patent Number: 5,573,950
[45] Date of Patent: Nov. 12, 1996

[54] CASSETTE FOR DISPOSABLE MICROORGANISM CULTURING MEDIA AND AUTOMATED SCANNING SYSTEM

[75] Inventors: Josef A. Graessle, Kaarst; Werner R. Schwarz, Leverkusen; Theo N. Wildt, Titz, all of Germany

[73] Assignee: Minnesota Mining and Manufacturing Company, St. Paul, Minn.

[21] Appl. No.: 240,846

[22] Filed: May 11, 1994

[51] Int. Cl.⁶ .................................................. C12M 1/34
[52] U.S. Cl. .................... 435/287.3; 435/288.7; 435/808; 435/809; 422/65; 422/104; 211/41
[58] Field of Search ............................. 435/289, 34, 38, 435/30, 291, 808, 809, 286.2, 287.1, 287.3, 288.3, 288.7, 305.1, 305.4; 422/63–65, 104; 359/391, 393, 394; 211/50, 59.4, 59.2, 55, 135, 150, 40, 41; 221/134, 197; 312/9.11, 9.26, 9.32, 9.48, 9.55, 9.56, 50; 414/222, 223; 100/194, 196, 202; 382/128, 129, 133

[56] References Cited

U.S. PATENT DOCUMENTS

| Re. 30,595 | 4/1981 | Covington et al. | 422/63 |
|---|---|---|---|
| 1,137,389 | 4/1915 | Evans | 312/9.56 |
| 3,851,972 | 12/1974 | Smith et al. | 356/72 |
| 4,118,280 | 10/1978 | Charles et al. | 250/328 |
| 4,565,783 | 1/1986 | Hansen et al. | 435/299 |
| 4,720,463 | 1/1988 | Farber et al. | 435/291 |
| 4,761,075 | 8/1988 | Matsushita et al. | 356/39 |
| 4,807,984 | 2/1989 | Kurimura et al. | 350/529 |
| 5,122,342 | 6/1992 | McCulloch et al. | 422/65 |
| 5,266,272 | 11/1993 | Griner et al. | 422/65 |
| 5,271,896 | 12/1993 | Jakubowicz et al. | 422/63 |
| 5,403,722 | 4/1995 | Floeder et al. | 435/39 |

FOREIGN PATENT DOCUMENTS

WO95/16768   6/1995   WIPO .............................. C12M 1/34

*Primary Examiner*—William Beisner
*Attorney, Agent, or Firm*—Gary L. Griswold; Walter N. Kirn; Paul W. Busse

[57] ABSTRACT

An apparatus for counting microorganism colonies on at least one disposable microorganism culturing medium having a substantially planar substrate. The apparatus is adapted to interact with a cassette holding a number of similar substrates at once. The apparatus includes an imaging device capable of detecting colonies on the substantially planar substrate, a cassette positioning device for moving the cassette so that the substrates supported within the cassette are moved sequentially into a predetermined position relative to the imaging device, and an ejecting device for ejecting a substantially planar substrate in turn from the cassette when that substrate is in the predetermined position from the cassette and into an imaging position adjacent the imaging device. Suitable cassettes and a method for counting colonies on substrates supported within a cassette are also disclosed.

11 Claims, 10 Drawing Sheets

Fig. 9

CASSETTE FOR DISPOSABLE MICROORGANISM CULTURING MEDIA AND AUTOMATED SCANNING SYSTEM

TECHNICAL FIELD

This invention relates to a method and apparatus for queuing and moving multiple similar objects for imaging, particularly to allow counting the number of distinct elements in the images so obtained. In particular, it relates to microbiological testing, and more particularly to improvements in the handling and reading of disposable microorganism culturing devices.

BACKGROUND OF THE INVENTION

Different methods and devices are known for counting microorganism colonies in, for example petri dishes or in thin film culture plate devices such as PETRIFILM™, manufactured by 3M of St. Paul, Minn. In the latter case, such devices have a very thin layer of growth medium, making all colonies visible with surface illumination. Manual counting of colonies on such media by trained laboratory personnel is well-known; typically a film will be inoculated and marked as to the source of the inoculant, stacked together with similar samples, and placed into an incubator. A manual inspection and counting is performed after a period of 12 to 24 hours. This method has known disadvantages, particularly the costs associated with the use of skilled technicians to perform the time-consuming task of manual counting, as well as the limited accuracy of the counts achieved.

Also desirable in the matter of microbiological counting is the early detection of colonies, particularly when food products are being tested. If the samples indicate excessive contamination, the product must often be discarded. Reliable early detection of excessive contamination in the range of 6 to 12 hours after inoculation would be welcomed by manufacturers because it would allow them to identify contaminated products early in processing, thereby avoiding additional expenses incurred in processing product that will be discarded and possibly contaminating additional product by running it through contaminated processing equipment.

International Publication No. WO 94/26870, which is hereby incorporated by reference, discusses improvements in colony counting in e.g. disposable microorganism culturing media having a substantially planar substrate. These include scanning and imaging the inoculated surface more than once and processing the images to produce a scaled time lapse image. Processing this scaled time lapse image allows the identification of hit pixels which can be clustered to identify the appearance of colonies. Thus early indication of colony growth can be obtained.

U.S. Pat. No. 5,403,722, which is also incorporated by reference, discloses a method and an apparatus for automated counting. However, a limitation on the apparatus disclosed therein is the physical properties of the disposable microorganism culturing media. Optimally, the art could wish for a more robust handling of the planar substrates, which have to be manipulated as a loose pile.

International Publication No. WO 95/16768, which is also incorporated by reference, discloses a specialized tool for handling disposable media under automatic control. The apparatus has an imaging means for detecting colonies on the disposable media, which media are contained within individual holders. Cooperating with the imaging means is a holder positioning means for storing and queuing one or more of the holders. The holder positioning means is adapted for moving the holders sequentially into a predetermined position relative to the imaging means so that images can be obtained. While this system provides a very accurate early detection, it is more complicated and expensive than is required in all industries where microbiological assays are performed.

OTHER BACKGROUND ART

For a more complete description of disposable devices for culturing microorganism such as PETRIFILM™ disposable thin film culture plates, the reader is directed to U.S. Pat. No. 4,565,783 to Hansen et al., which is hereby incorporated by reference. Additional chemistries which are preferred for use with the imaging means contemplated by the present invention are more completely described in U.S. Pat. No. 5,364,766. That copending and coassigned application is also hereby incorporated by reference.

SUMMARY OF THE INVENTION

The present invention addresses the above identified limitations in the art by allowing planar substrates to be more accurately monitored under automatic control. In one aspect, the invention might be considered as an apparatus for counting microorganism colonies on at least one disposable microorganism culturing medium having a substantially planar substrate, the substrate adapted to fit within and be supported by a cassette. Using a cassette this way provides a convenient way to handle a number of substrates at once. The apparatus itself includes an imaging means capable of detecting colonies on the substantially planar substrate. It also includes a cassette positioning means for moving the cassette so that the substantially planar substrates supported within the cassette are moved sequentially into a predetermined position relative to the imaging means. Finally, there will be an ejecting means for ejecting a substantially planar substrate in turn from the cassette when that substrate is in the predetermined position from the cassette and into an imaging position adjacent the imaging means.

In some embodiments, the imaging means and its associated electronics provides an indicating signal as to whether or not a substantially planar substrate matches predetermined criteria chosen by the operator of the apparatus. This indicating signal may be transmitted to the operator directly via panel displays or printouts, or it may be logged electronically for later retrieval. In addition, the signal may be used to control a means for sorting the substantially planar substrates physically into two or more categories based on the indicating signal.

Other embodiments of the apparatus may be adapted to work with a particular type of cassette. This cassette will be adapted for supporting a plurality of substantially planar substrates, and can generally be described as an enclosure having two ends. Between the two ends, and disposed within but not rigidly affixed to the enclosure, will be a plurality of plates. There will be some means for retaining the plates within the enclosure. This could be, for example, rigid strips tying the edges of the ends together. More conveniently, the ends can be tied together by a number of rods extending between the ends. Mounted as a stack on these rods will be the plates, each having holes therein to permit the mounting, with the rods passing though the holes. There will be some means for supporting the plates at least some minimum distance apart from each other. This allows the ejection means to move each substrate in turn robustly, and allows an operator to readily separate the plates when loading the cassette with substrates. This may conveniently be accomplished by placing annular spacers, such as thin washers, on the rods between the plates. This is particularly appropriate when the plates are fabricated by die cutting from polymeric sheet stock. Alternatively, projections can be attached or molded onto to the plates to stand them off in the required fashion.

In preferred embodiments, the plates each have a cut-out section in one side, and are mounted with these cut-out sections one above another. As will be detailed more specifically below, such an arrangement facilitates the ejecting means acting on the substrates as the positioning means moves the cassette.

In a second aspect, the invention may be considered to be a method of counting microorganism colonies on at least one disposable microorganism culturing medium having a substantially planar substrate, said method comprising the steps of:

(a) providing a cassette adapted to support a plurality of substantially planar substrates;

(b) moving said cassette so that the substantially planar substrates supported therein are moved sequentially into a predetermined position;

(c) ejecting sequentially the substantially planar substrates in said predetermined position from the cassette into an imaging position; and (d) imaging the substantially planar substrates in said imaging position.

Optionally, the method may further include the step of sorting the substantially planar substrate into categories based on the results of the imaging step.

In a third aspect, the invention may be considered to be related to the cassette described above per se, with its special utility in supporting the substantially planar substrates.

The invention provides an apparatus for automatically counting colonies during microbiological testing.

A feature of the invention is the use of a cassette holding a number of substantially planar substrates at once, which cassette is inserted into the reading apparatus. The substrates are then ejected and imaged one at a time as their location within the cassette passes by a predetermined position.

An advantage of the invention is that a number of substrates can be handled and imaged automatically as a group, with the handling of the thin, flimsy substrates being accomplished robustly.

Another advantage of the invention is that the apparatus can deal with a cassette which is not totally filled; rather it can handle, without special operator intervention, any arrangement of the loading of the cassette.

BRIEF DESCRIPTION OF THE DRAWINGS

A more complete understanding of the invention and its advantages will be apparent from the Detailed Description taken in conjunction with the accompanying Drawings, in which.

DETAILED DESCRIPTION

Figure 1:
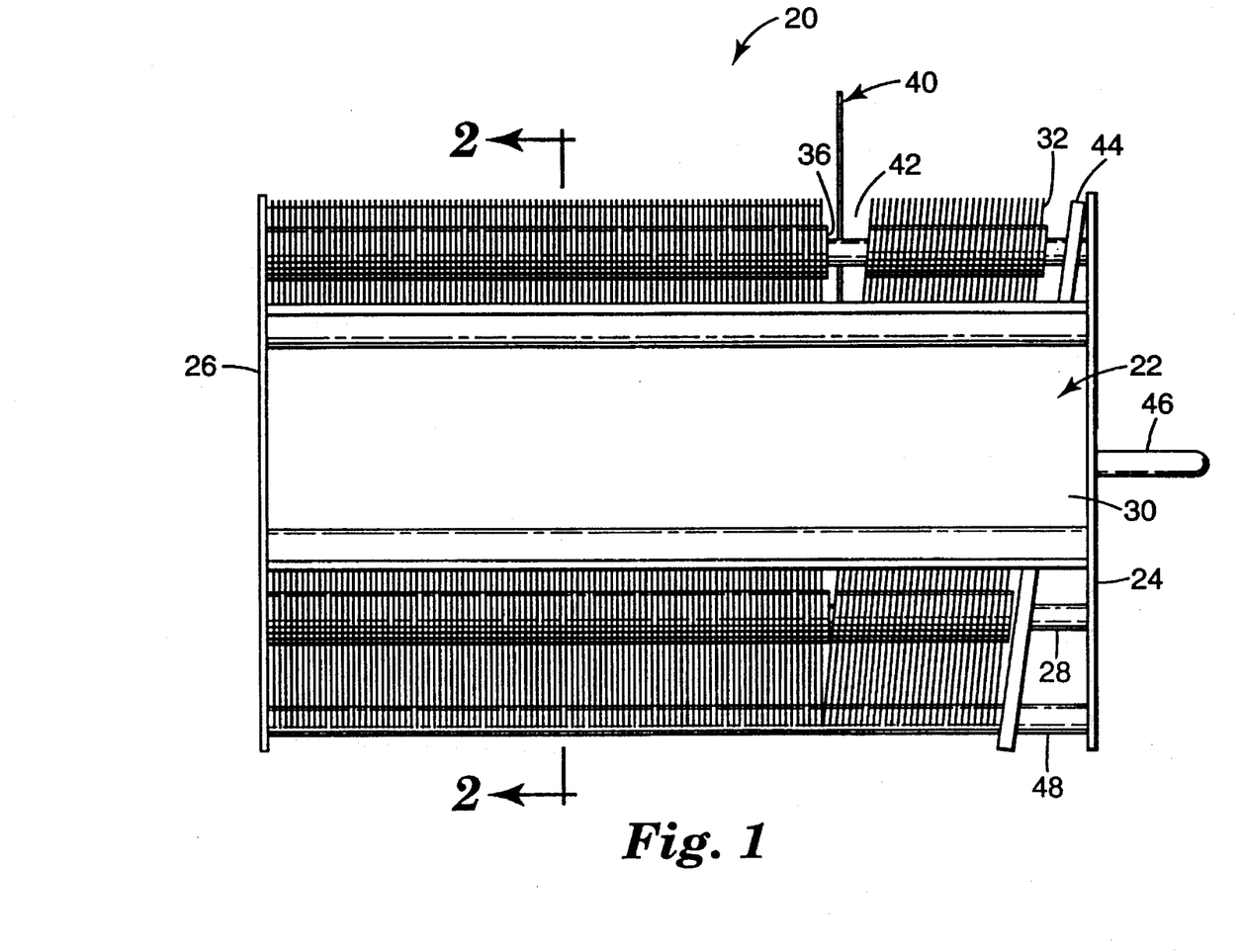
FIG. 1 is a side view of a cassette according to the present invention, suitable for supporting a disposable microorganism culturing medium having a substantially planar substrate.

Referring now to FIG. 1, a side view of a cassette according to the present invention, suitable for supporting a disposable microorganism culturing medium having a substantially planar substrate, is illustrated. The cassette 20 includes an enclosure 22 having a top end 24 and a bottom end 26. The ends 24 and 26 are held rigidly together by several rods 28, and optionally for more structural strength, one or more side walls 30. A number of plates 32, each having a plurality of holes 34 therein, are mounted within the enclosure 22 with the rods 28 passing through the holes 34. The plates 32 are kept a minimum distance apart from each other by means of annular spacers 36, also mounted on the rods 28. In the illustration, a disposable microorganism culturing medium having a substantially planar substrate 40 is shown being loaded into the cassette 20. The cassette 20 is lying on its back, and in this position, the plates 32 can be manually opened to the correct place for substrate insertion. This action is facilitated by the fact that the plates 32 are held apart by the spacers. 36, which allows a fingertip to separate them, and by the fact that the size of the holes 34 in the plates 32 is sufficient to allow the plates to flop over somewhat and provide a gap 42 as illustrated in this figure. Insertion of a substrate 40 is further enhanced if the plates 32 are made of a thin, but bendable, polymeric material. In preferred embodiments, there will be a stack weight 44 mounted on the rods 28 at the top of the stack of plates 32 to close gaps and provide a predictable downward force on the stack of plates when the cassette is held upright. Such a downward force facilitates the action of the ejecting means as will be described below. For the convenience of the operator, a handle 46 may be attached to the top end 24.

Figure 2:
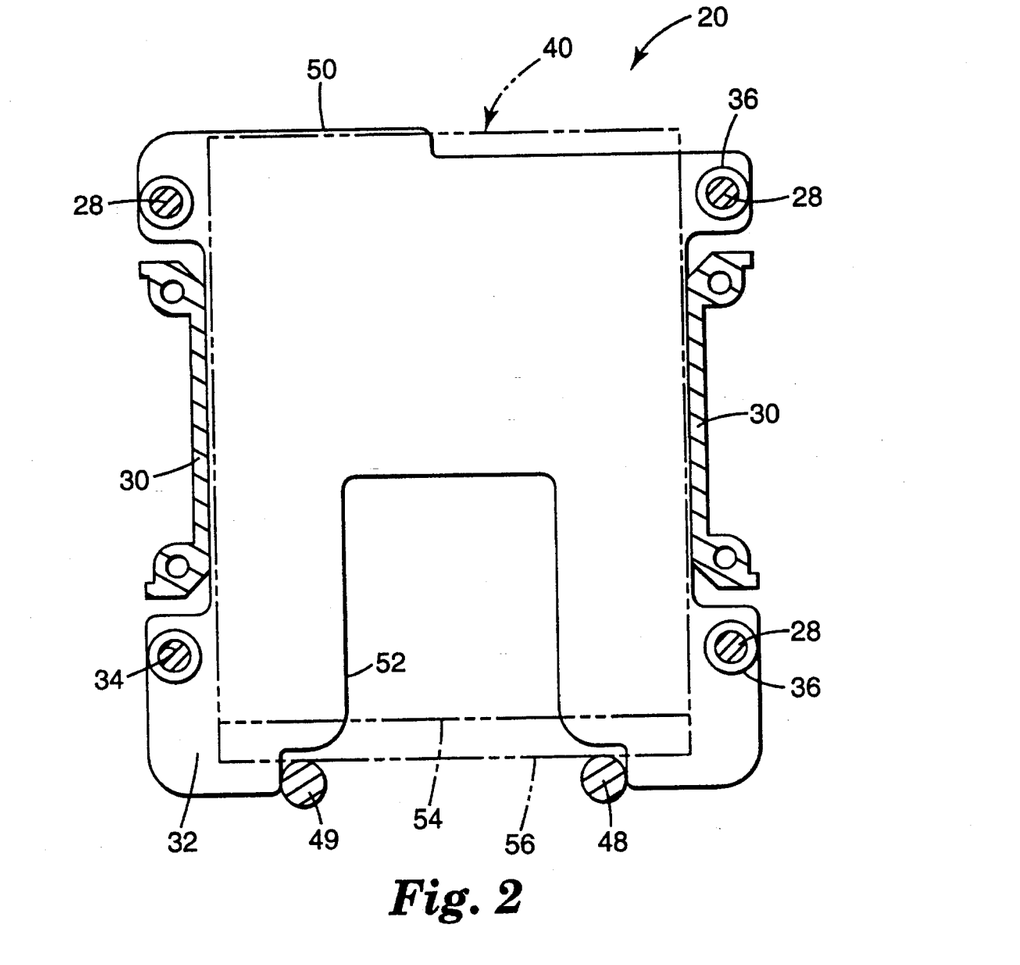
FIG. 2 is a top section view taken along section lines 2—2 in FIG. 1.

Referring now to FIG. 2, a top section view taken along section lines 2—2 in FIG. 1 is illustrated. For clarity, in this view a substrate 40 is illustrated in phantom lines showing a typical placement when loaded within the cassette 20. In this view it is more readily seen that besides rods 28 which pass through holes 34 in plates 32, there may also conveniently be guide rods 48 and 49 positioned at the rear of the cassette 20 to limit how far the substrate 40 can go when inserted from the front into the cassette. It is also convenient to provide a projecting tab 50 on the front of each plate to make separating the plates for the insertion of the substrates as easy as possible for the operator.

It will also be seen that the plate 32 has a cut-out section 52 in the back side. As will be noted with more specificity later, the ejecting means resides partially within the space defined by the cut-out sections when the cassette 20 is engaged with the positioning means in the counting apparatus.

Preferred substrates suitable for use with this apparatus will have a base sheet 54, and a cover sheet 56 which is slightly longer. This arrangement not only makes the substrate easier to handle during inoculation, but in the context of the present invention helps the action of the ejecting means be more certain.

Figure 2A:
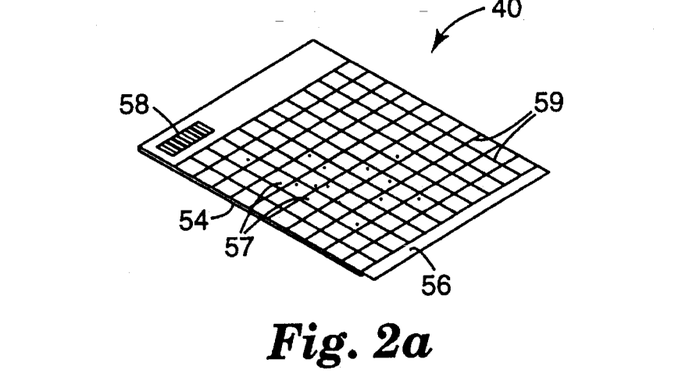
FIG. 2a is a top perspective view of a disposable microorganism culturing device such as PETRIFILM™ having a number of colonies located thereon.

Referring now to FIG. 2a, a disposable microorganism culturing device 40, such as the PETRIFILM™ product described above, is illustrated. The device includes a base sheet 54 having microorganism colonies 57 located on its surface. Once again, it is to be noted that the cover sheet 56 extends further than the base sheet 54. In a preferred embodiment, the substrate 40 also preferably includes a barcode 58 at its upper edge for identifying individual samples. PETRIFILM™ products also typically include a series of grid lines 59 which are useful for manual counting of colonies. Although the preferred apparatus is designed for use with PETRIFILM™ products, it will be understood that any similar product having a substantially planar substrate with nutrients adhered to its surface for the culturing of microorganisms could be used in place of PETRIFILM™ products.

Figure 3:
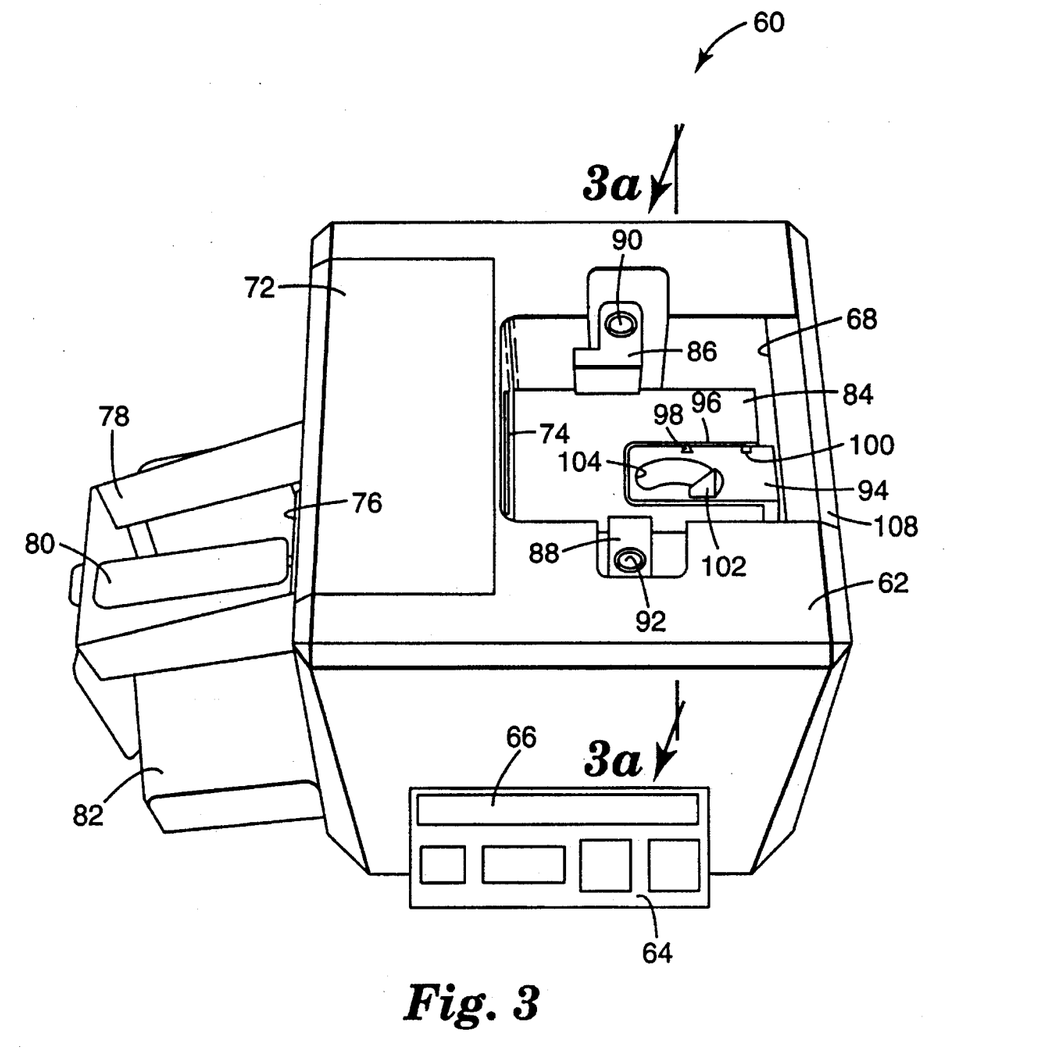
FIG. 3 is a top perspective view of an embodiment of the counting apparatus of the present invention, adapted for use with the cassette of FIG. 1.

Now referring to FIG. 3, a top perspective view of an embodiment of the counting apparatus 60 of the present invention, adapted for use with the cassette of FIG. 1, is illustrated. The bulk of the apparatus is protected by an enclosure 62, and mounted on the enclosure is a control panel 64 and a display screen 66 to allow operating commands to be entered by the user, and for data to be displayed. A recess 68 is provided in the top of the enclosure 62, adapted to receive a cassette 20 of the type described above. The imaging means 70 (not seen) and its associated electronics are located under access cover 72. Substrates which are ejected from the cassette are delivered to the imaging means 70 through slot 74, and discharged from the imaging means through slot 76. Once discharged from the slot 76, the substrate falls into a sorting cradle 78, and onto a rotatable platform 80. A signal from the imaging means cues a mechanism which can tilt the rotatable platform 80 one way or the other, dropping each substrate into one side or the other of a generally W-shaped bin 82, thus sorting the substrates into categories based on the results of the imaging step. For example, the electronics may be set to sort the substrates into the categories of minimally acceptable and non-acceptable colony counts according to a criterion chosen by the operator. Alternatively, the sorting criterion might be successfully scanned and not successfully scanned substrates. Other mechanisms which can sort the substrates into more than two categories are also contemplated within the definition of the invention.

Within recess 68 is a means to position the cassette as required, including a movable stand 84 which has a pair of threaded trucks 86 and 88. The trucks are adapted to engage a pair of threaded shafts 90 and 92, so that synchronously rotating the shafts causes the trucks, and hence the stand 84 to move up or down. Housed in a central column 94 within the recess 68 is the means for ejecting a substrate out of the cassette and towards slot 74. This column 94 fits within a cut-out portion 96 in stand 84, so that the stand can move downwards within the recess 68 from the starting position here illustrated. As it does so, column 94 begins to enter the space defined by the cut-out sections 52 in plates 32.

During the operation of the counting apparatus 60 to count colonies on substrates contained within a cassette 20, the stand 84 is moved to its uppermost position by sending an appropriate signal to the motor controlling the rotation of threaded shafts 90 and 92. Then the cassette beating the substrates of interest is placed on stand 84, and the read operation started. The threaded shafts 90 and 92 begin to rotate so that the stand 84 is lowered relative to column 94. As column 94 begins to enter the space defined by the cut-out sections 52 in plates 32, eventually a sensor lever 98 will contact the lowest substrate within the stack of plates 32. This lightly spring loaded sensor lever 98 will depress, signalling the motor controller to temporarily halt the rotation of the threaded shafts. Attached to the sensor lever 98 is an extended arm 100 which will signal the motor controller to stop the rotation of the threaded shafts when the stand 84 is being raised and arrives at its uppermost position.

At the point when the actuation of sensor lever 98 halts the lowering of the movable stand 84 due to its contacting the lowermost substrate 40 in the stack, pusher arm 102 will be under the extended edge of its cover sheet 56 but behind the edge of its base sheet 54. Thus the cover sheet 56 of the lowermost substrate 40 shields the pusher arm 102 from accidentally snagging the next substrate upwards and causing a misfeed, when as next occurs, the pusher arm 102 moves in a circular fashion within curved slot 104 to eject the lowest substrate. The pusher arm 102 moves the substrate through slot 74 and into engagement with pinch rollers associated with the imaging means. Then the pusher arm 102 retracts backwards, and the threaded shafts 90 and 92 are activated again so that the next substrate in the stack within the cassette 20 can be located and the cycle started again. Eventually, all the substrates are read, and the stand 84 bottoms out near the bottom of recess 68 and contacts a limit lever 106 (seen in FIG. 4), notifying the electronics that the entire cassette has been read.

Figure 3A:
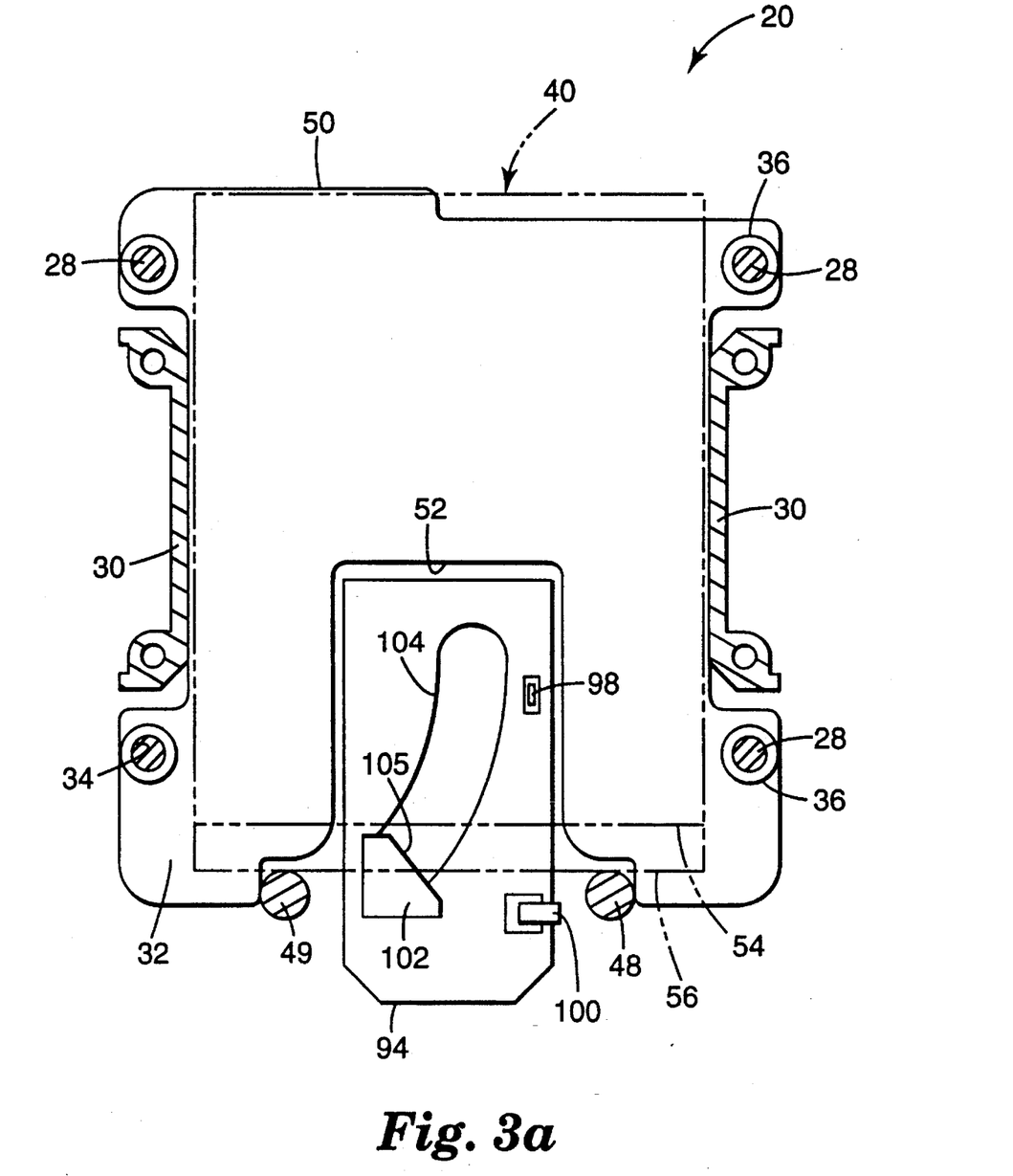
FIG. 3a is a horizontal cross-section detail view of the area of the top of a column housing the ejecting means, taken along the plane defined by the top of the column, when the cassette is mounted on a movable stand which forms part of the positioning means.

FIG. 3a is a horizontal cross-section detail view of the area of the top of column 94, taken along the plane defined by the top of the column, when the cassette 20 is mounted on the movable stand 84. As in FIG. 2, the substrate 40 is shown in phantom in order to visualize the structures on the top of the column 94 and their relationship to the lowest substrate in the stack of substrates within the cassette, and more readily illustrates how spring loaded sensor lever 98 will depress as the cassette 20 moves downwards and the substrate 40 contacts it. In this view it is also more readily appreciated how the leading edge of pusher arm 102 will be under the extended edge of cover sheet 56 but behind the edge of its base sheet 54. When commanded by the electronic controls of the apparatus, the pusher arm 102 moves in a arced fashion within curved slot 104, turning its flat leading edge 105 towards the substrate 40 as it moves so that an even pressure is applied when the substrate is pushed into engagement with the pinch roller pair within slot 74.

Figure 4:
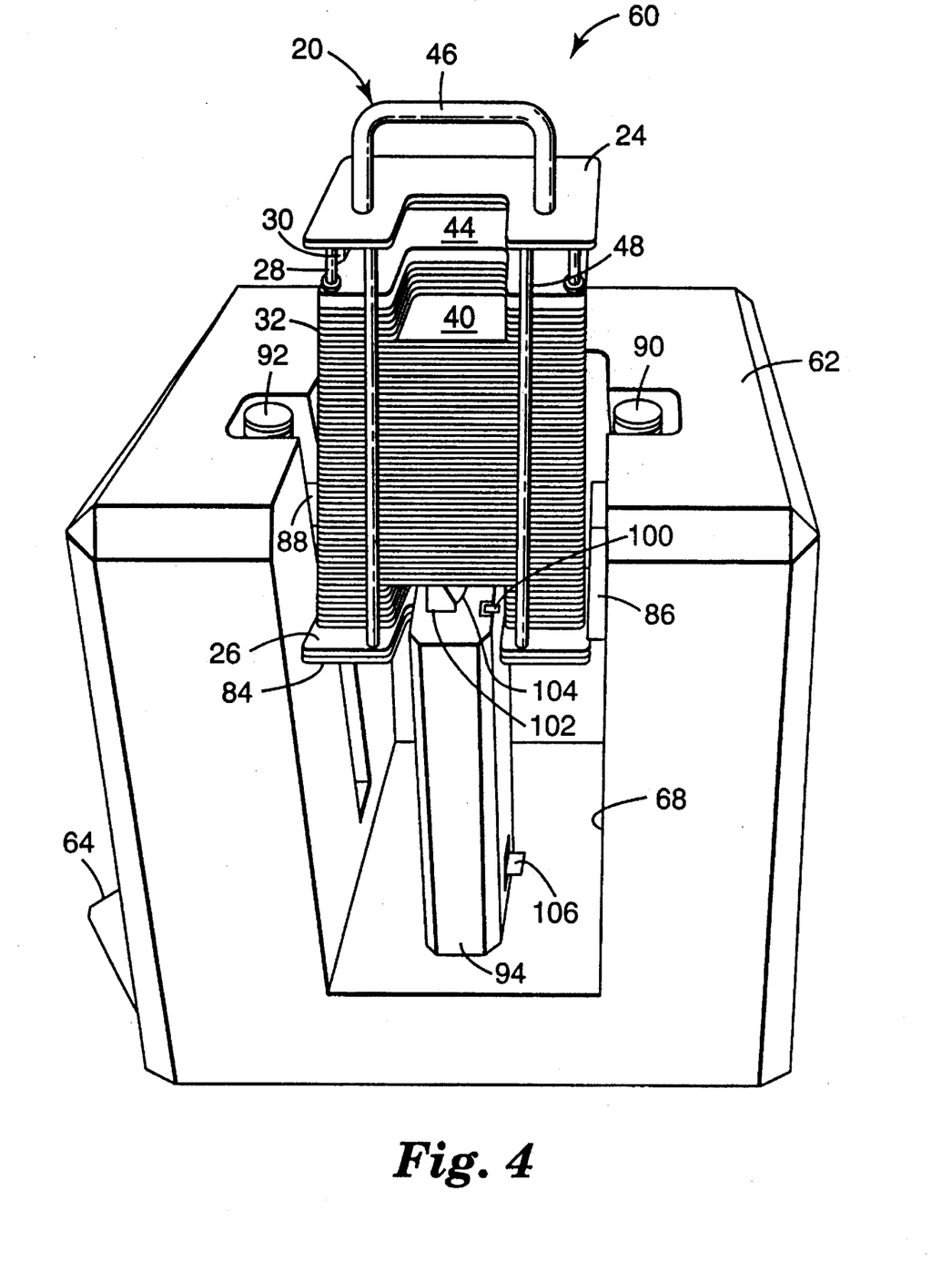
FIG. 4 is side perspective view of the apparatus of FIG. 3, with a side panel removed to more readily display the interaction between a cassette and the cassette positioning means.

Once again with reference to FIG. 3, the recess 68 is closed on one side with a side panel 108 for the convenience of the maintenance technician. Referring now to FIG. 4, a side perspective view of the apparatus of FIG. 3, with side panel 108 removed to more readily display the interaction between a cassette and the cassette positioning means, is illustrated.

Figure 5:
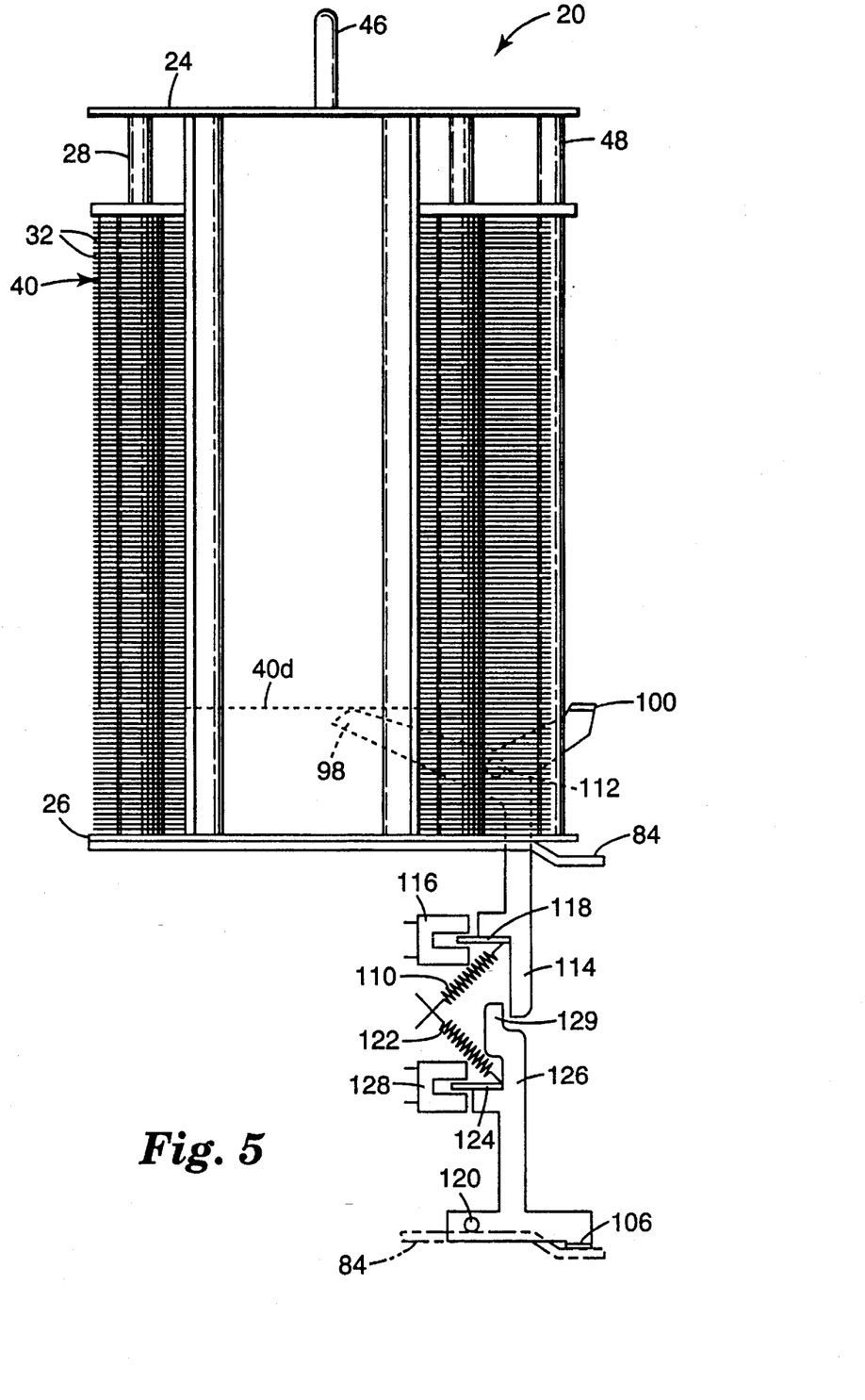
FIG. 5 is a side view of a cassette interacting with sensor elements provided to control the cassette positioning means.

Referring now to FIG. 5, a side view of a cassette interacting with the sensor elements usually housed within column 94, with the column removed for clarity, is illustrated. The cassette 20 is supported by stand 84, which has been lowered to the point that the lowest substrate 40 in the stack of substrates in the cassette 20 (designated as 40d) is just contacting sensor lever 98. As lowering of the stand continues, the sensor lever 98 will depress slightly against the urging of extension spring 110 and pivot about its pivotal mounting 112, which is fixed to column 94. The lower leg 114 of the sensor lever will move away from optical switch 116. When the light shield 118 is withdrawn from optical switch 116, the controlling electronics are signaled to halt the lowering of the stand 84 and to activate the pusher arm 102. In this way, all of the substrates 40 are read in turn until the stand 84 contacts limit lever 106, (this position is shown in phantom) which then pivots about its pivotal mounting 120 and against the urging of extension spring 122 to withdraw light shield 124 on upper leg 126 from optical switch 128. This also causes extended portion 129 to move lower leg 114 away from optical switch 116, which halts the decent of the stand 84. The activation of optical switch 128 further signals the electronics to return stand 84 to its uppermost starting position.

Figure 6:
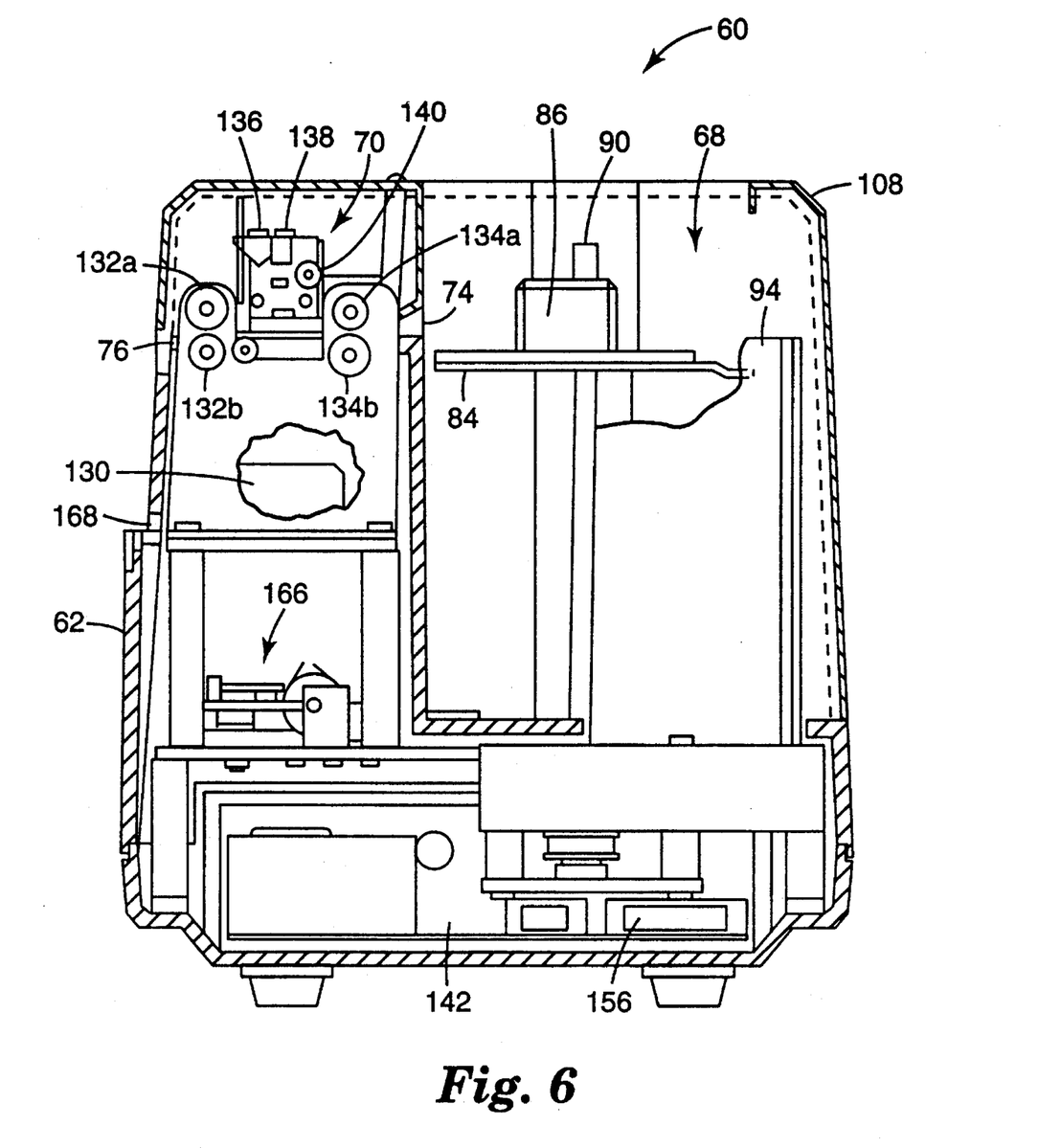
FIG. 6 is a cross-section side view of the apparatus, particularly high-lighting a preferred arrangement for the imaging means.

Referring now to FIG. 6, a cross-section side view of the apparatus 60 is illustrated, particularly high-lighting a preferred arrangement for the imaging means 70. The counting apparatus 60 includes a motor 130 which is preferably a DC stepping motor. Motor 130 is operably connected to-roller pairs 132a,b and 134a,b to move a substrate 40 which has entered the enclosure 62 through slot 74 through the imaging means 70 for scanning. The stepping motor 130 provides accurate incremental movement of the substrate 40 though the imaging means 70. The preferred imaging means 70 includes a linear LED array 136 aimed at the substrate 40. The preferred LED array is Model No. LT4665E manufactured by Sharp Corporation. This LED array is particularly useful because it produces light in wavelengths that neutralize a grid array placed on one version of the PETRIFILM™ product to facilitate manual counting. A similar effect could be duplicated with light sources producing other wavelengths by using a reddish-yellow filter (Wratten filter #9 or Corion LL-550-S-4385) between the light source and a counting sensor 138.

The preferred LED array 136 is also useful for the present application because the intensity of the light produced across the array is substantially uniform, which aids in the accuracy of the apparatus.

Located above substrate 40 in the preferred counter is a linear array of SELFOC lenses 140, Model No. SLA-12-TC43A6, manufactured by Nippon Sheet Glass Co. This rod lens array 140 is widely used in facsimile machines as well as some photocopying equipment. Above the SELFOC lens array is a linear CCD sensor array 138, preferably Model No. TCD 127AC, manufactured by Toshiba Corporation.

Figure 7:
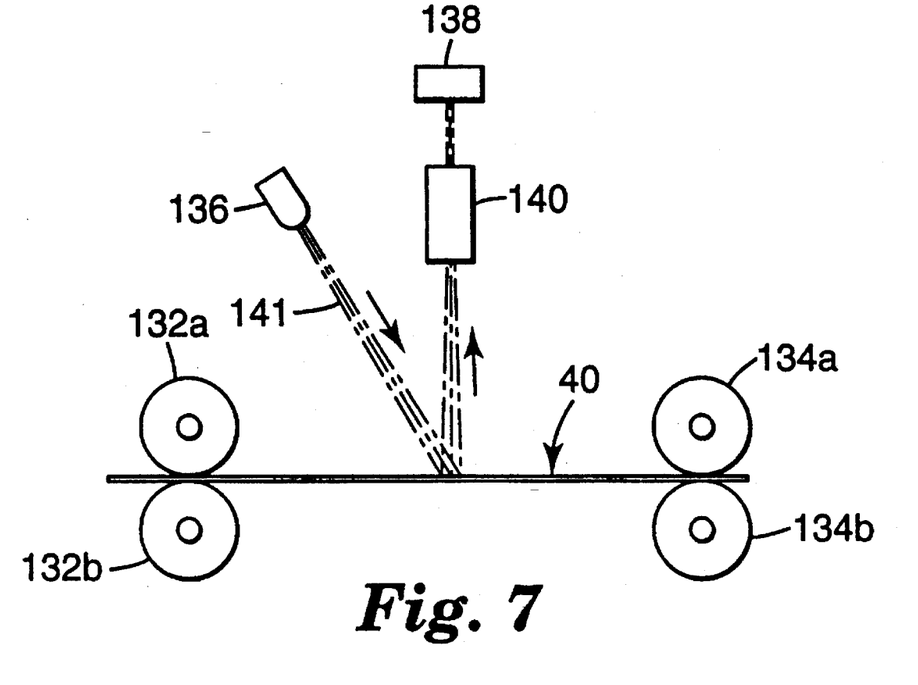
FIG. 7 is an enlarged cross-sectional side view of the scanning area of the preferred apparatus.

FIG. 7 is an enlarged view of the scanning area of the preferred apparatus. As shown there, LED array 136 produces light 141 which reflects off of substrate 40 and is at least partially reflected through the SELFOC lens 140 which focuses the light on the CCD image sensor 138. Rollers pairs 132 and 134 are used to move the substrate 40 through the scanning area. As discussed above, the rollers are preferably connected to stepping motor 130 for accurate incremental movement of the substrate 40 through the scanning area.

Figure 8:
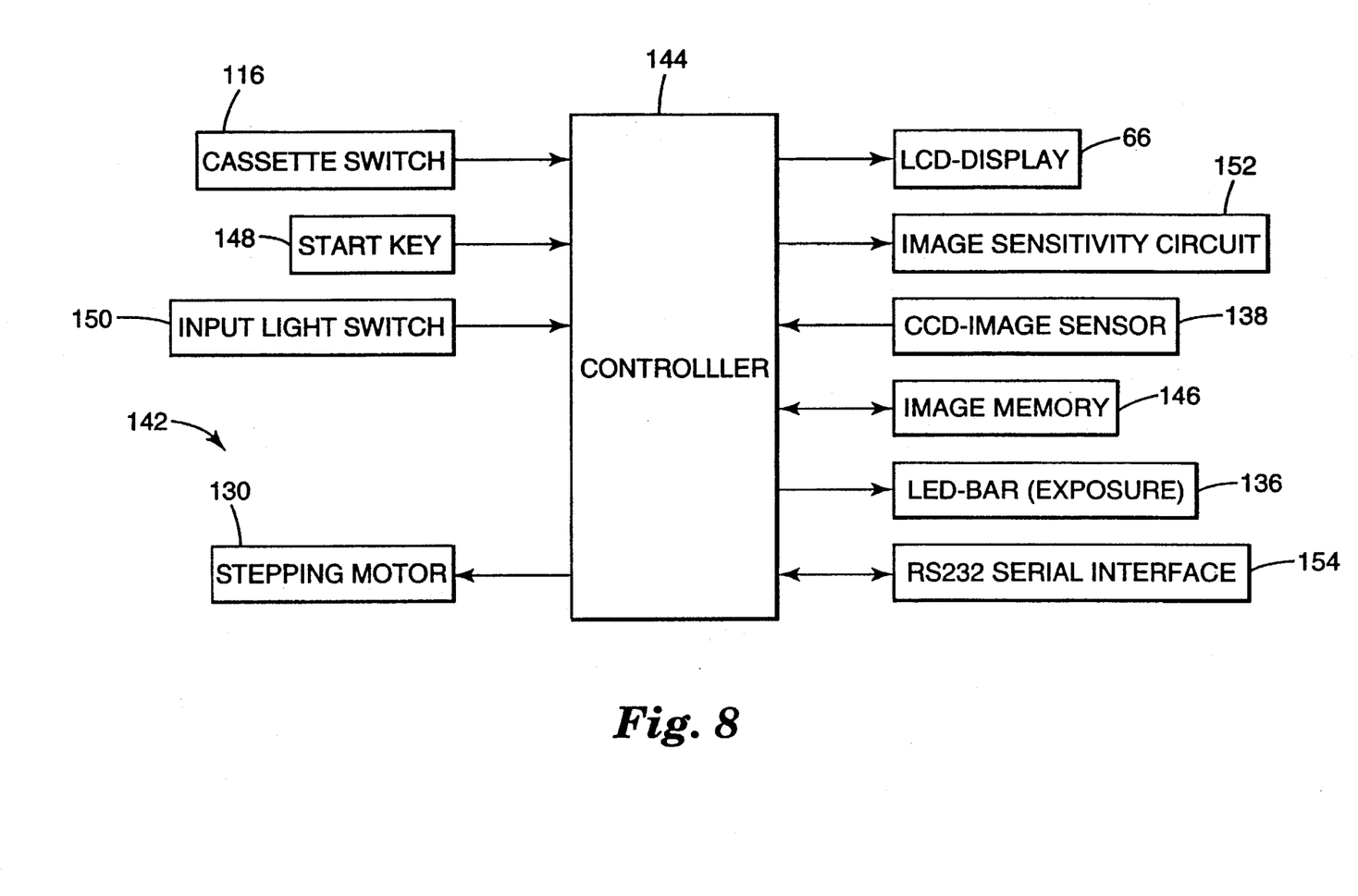
FIG. 8 is a block diagram illustrating the control system of the present invention.

FIG. 8 is a block diagram illustrating the preferred control system of the present invention. As illustrated, the CCD image sensor 138 is connected to the control circuit 142 based around a microprocessor 144. A preferred control circuit 142 will incorporate a CMOS microcontroller, Model No. 80C451, manufactured by Signetics.

Data from the CCD image sensor 138 is stored in the image memory 146 also connected to the microprocessor 144. The LCD display 66 is used to provide messages to the operator and prompt actions by the same. The cassette switches 116 and 128 are used to indicate the condition and position of the cassette as discussed above in connection with FIG. 5. The start key 148, part of control panel 64, is used to begin the process of moving the cassette 20, bringing each substrate 40 in turn into the predetermined position, and ejecting the substrate into the imaging position and performing the imaging step. An input light switch 150 may optionally be present, used to indicate whether a substrate 40 has actually been moved into the imaging position, thus identifying misfeeds.

The stepping motor 130 is used to incrementally advance substrates 40 through the imaging position and is operably connected to the rollers 132a,b and 134a,b as shown in FIGS. 6 & 7. The rollers are preferably gear-driven, although any suitably accurate connection method can be used.

The LED bar array 136 is used to illuminate the surface of the substrate 40 and any objects on it for sensing by the CCD image sensor 138. The CCD image sensor 138 is used to detect objects from the reflected light. The image sensitivity circuit 152 is used to adjust sensitivity of the CCD image sensor 138 to a level below which a blank substrate 40 will not trigger the image sensor. An advantage of image sensitivity circuit 152 is that it automatically adapts each element of CCD image sensor 138 to differences in the background image caused by variations due to different substrate materials, variations in light density across the surface of each substrate, and variations in the manufacturing tolerances of the CCD sensor.

The image memory 146 is used to store data from the CCD image sensor 138 and is used to detect the number of distinct objects on the surface of the substrate 40 using an appropriate algorithm. The RS-232 serial interface 154 is used to provide communication between the present invention and a computer or other electronic device for purposes such as long-term data storage and analysis.

To begin the process, the counting apparatus 60 is powered up and the LCD display 66 indicates to the operator that a cassette 20 containing a number of substrates should be loaded into the onto the movable stand 84. In some embodiments, the operator may be prompted to make sure the lowermost position in the cassette is loaded with a blank (empty) substrate. The blank substrate is used to adjust the sensitivity of the CCD image sensors via the image sensitivity circuit 152 in order to avoid errors in the detection process. Once the cassette is loaded, the operator begins the counting operation, for example by pressing a start key 148, and the read cycle begins as discussed above.

The microcontroller 144 may also interact with the positioning means by having control over a motor 156 used to control the drive of threaded shafts 90 and 92. The exact programming required depends on the devices chosen, but the methods required are well known to those conversant with the art of programming embedded controllers. Any suitable machine vision algorithm may be used to analyze the scanned image, but the algorithm discussed in U.S. Pat. No. 5,403,722, incorporated by reference above, is considered particularly preferred.

Figure 9:
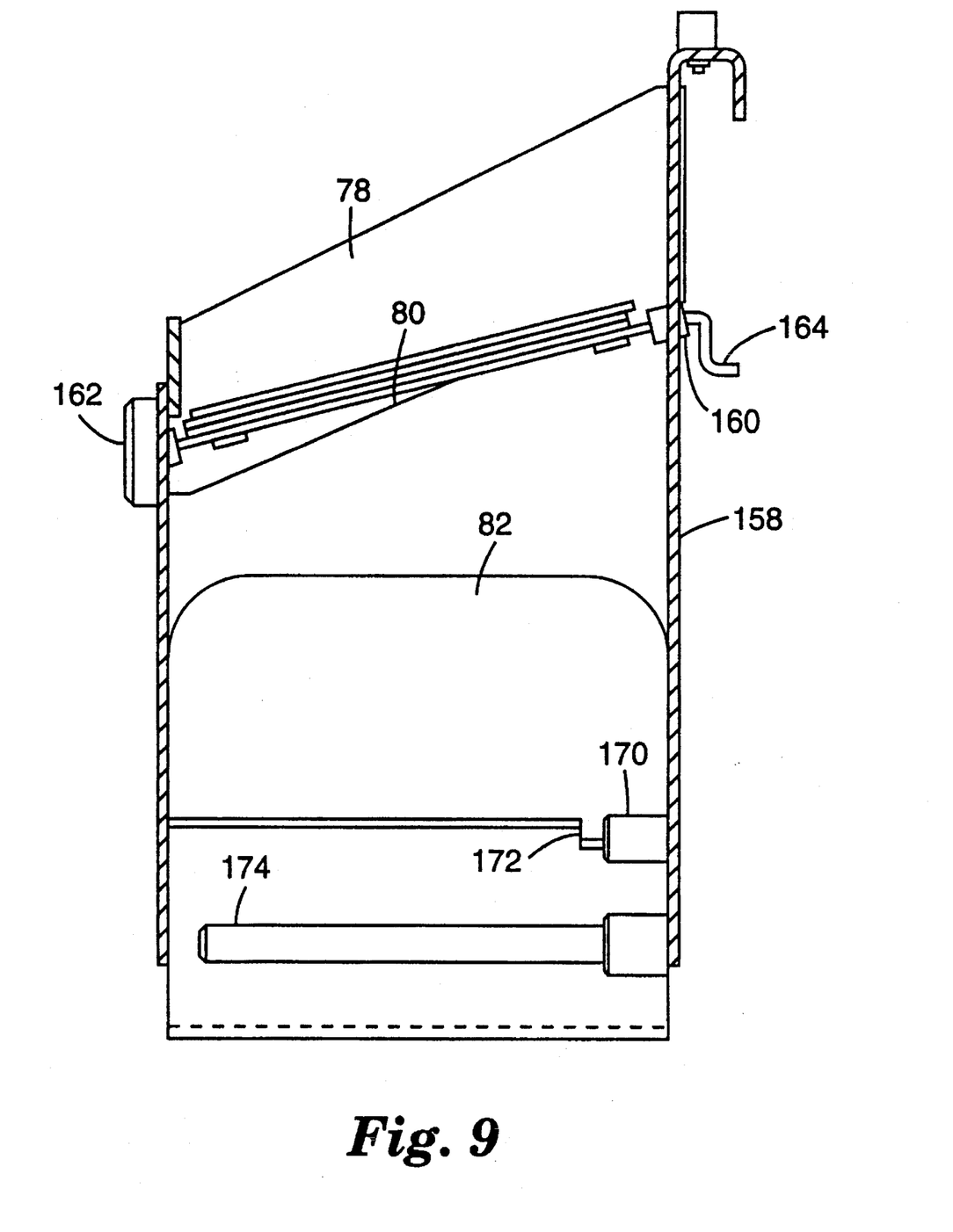
FIG. 9 is a cross-section side view sectioned a vertical plane of symmetry through an exemplary sorting mechanism.

In preferred embodiments, the roller pair 132a and 132b eject the just scanned substrate 40 through slot 76 and into a sorting mechanism. Referring now to FIG. 9, a cross-section side view sectioned a vertical plane of symmetry through an exemplary sorting mechanism is illustrated. Conveniently, the sorting cradle 78 is attached to a bracket 158 which is adapted to removably engage enclosure 62 near slot 76. The bracket 158 supports rotatable platform 80 on a pair of bearings 160 and 162. Rotatable platform 80 conveniently has an extension rod 164 which engages tilt mechanism 166 through a hole 168 in the enclosure 62 when the bracket 158 is mounted on the enclosure so that mechanism 166 can tilt the rotatable platform 80 one way or the other, dropping each substrate into one side or the other of a generally W-shaped bin 82. These elements are sized so that the substrate cannot fall directly down beyond rotatable platform 80 while platform 80 is in its horizontal, neutral position. Depending on the results of the scan performed by the imaging means 70 the control circuit 142 will cue a tilt mechanism 166 which can tilt the rotatable platform 80 one way or the other, thus sorting the substrates 40.

Conveniently, the bracket 158 will have a stud 170, which fits into an aperture 172 in W-shaped bin 82, and a pair of extended rods 174, positioned to support the underside of the bin when the stud is in the aperture. This arrangement supports the bin 82 in a stable, but removable, fashion.

DESCRIPTION OF THE PREFERRED EMBODIMENTS

Cassettes suitable for use with the present invention can be fabricated from numerous materials, but the rigid structural components of the enclosure are conveniently formed from a metal such as aluminum by machining, or from thermoplastic polymers by injection molding. A certain amount of toughness in order to endure repeated handling by the operator and by the positioning means is desirable, so plastics such as polycarbonate are considered particularly preferred. Proper material selection for the plates helps to make a durable, yet easy to load cassette; sheet stock of polyetherimide, commercially available as ULTEM DL1648 from Cadillac Plastic, is considered preferred.

While certain embodiments of the present invention have been described in detail herein and as shown in the accompanying Drawings, it will be evident that various further modifications are possible without departing from the scope of the invention.

We claim:

1. An apparatus for detecting microorganism colonies on at least one disposable microorganism culturing medium having a substantially planar substrate, said apparatus comprising:

a cassette adapted for supporting a plurality of the substantially planar substrates, the cassette comprising (a) an enclosure having two ends;

(b) a plurality of plates, disposed within but not rigidly affixed to said enclosure;

(c) means for retaining said plates within said enclosure; and (d) means for supporting said plates at least a minimum distance from each other;

imaging means for detecting colonies on the substantially planar substrate;

cassette positioning means for moving said cassette so that the substantially planar substrates supported within said cassette are moved sequentially into a predetermined position relative to said imaging means; and ejecting means for ejecting a substantially planar substrate in said predetermined position from said cassette and into an imaging position adjacent said imaging means.

2. An apparatus according to claim 1 wherein each of said plurality of plates has a plurality of holes therein, and said means for retaining said plates within said enclosure of the cassette comprises a plurality of rods extending between said ends disposed within said holes in said plates.

3. An apparatus according to claim 1 wherein each of said plates has a cut-out section in one side, and wherein said ejecting means resides partially within the space defined by the cut-out sections when the cassette is engaged with said positioning means.

4. An apparatus according to claim 3 wherein said ejecting means comprises a pusher arm which moves from a retracted position to an actuated position during the ejection of the substrate from said predetermined position.

5. An apparatus according to claim 4 wherein when the substrates disposed within the cassette are of the type comprising a base sheet and a cover sheet which is slightly longer than said base sheet, movement of the cassette caused by said cassette positioning means causes said pusher arm to contact each substrate in turn in such a manner that the force exerted by the pusher arm on the substrate in said predetermined position when said pusher arm is ejecting the substrate from said predetermined position is entirely on said base sheet.

6. A cassette adapted for supporting a plurality of substantially planar substrates, comprising:

(a) an enclosure having two ends;

(b) a plurality of plates, disposed within but not rigidly affixed to said enclosure;

(c) means for retaining said plates within said enclosure; and (d) means for supporting said plates at least a minimum distance apart from each other when the cassette is oriented with the plates disposed horizontally.

7. An cassette according to claim 6 wherein each of said plurality of plates has a plurality of holes therein, and said means for retaining said plates within said enclosure of said cassette comprises a plurality of rods extending between said ends disposed within said holes in said plates.

8. A cassette according to claim 7 wherein said supporting means comprises a plurality of annular spacers disposed on said rods and between said plates.

9. A cassette according to claim 6 wherein said supporting means comprises projections attached to said plates.

10. A cassette according to claim 6 wherein each of said plates has a cut-out section in one side.

11. A cassette according to claim 6 wherein said plates are formed of a thin, bendable, polymeric material.

* * * * *